(12) United States Patent
Farris

(10) Patent No.: US 6,383,166 B1
(45) Date of Patent: May 7, 2002

(54) PLUNGERLESS SYRINGE: METHOD AND APPARATUS

(75) Inventor: Barry Farris, Zephyr Cove, NV (US)

(73) Assignee: Zephyr Cove, NV (US)

( * ) Notice: Subject to any disclaimer, the term of this patent is extended or adjusted under 35 U.S.C. 154(b) by 0 days.

(21) Appl. No.: 08/818,958

(22) Filed: Mar. 14, 1997

(51) Int. Cl.$^7$ ............................................. A61M 5/00
(52) U.S. Cl. ........................ 604/187; 604/212; 222/94
(58) Field of Search .................... 604/212–217, 604/122, 187, 185, 49, 190, 191, 403, 410, 200, 181; 222/92, 94, 95, 96, 97, 129, 130, 147

(56) References Cited

U.S. PATENT DOCUMENTS 5,102,398 A * 4/1992 Farris ........................ 604/212
5,370,626 A * 12/1994 Farris ........................ 604/187
5,509,906 A * 4/1996 Poynter ....................... 604/216
5,538,506 A 7/1996 Farris et al.

OTHER PUBLICATIONS

Principals and Practice of Intravenous Therapy, 1987, pp. 53 and 55, Little Brown and Company—Fourth ed.

* cited by examiner

Primary Examiner—Angela D. Sykes
Assistant Examiner—Ronald Stright
(74) Attorney, Agent, or Firm—Bernhard Kreten

(57) ABSTRACT

A Blow/Fill/Seal, or injection molded plungerless syringe having a body portion, a fluid outlet at one end and an air passageway at an opposite end, extending from a back wall leading to a chamber having the ability to receive all syringe air plus some liquid. The air passageway communicates with the air chamber to trap all gas into the air chamber after docking with syringe needle or catheter at the fluid outlet. Air from the docked devices pass through the liquid and is trapped out of the fluid passage.

6 Claims, 3 Drawing Sheets

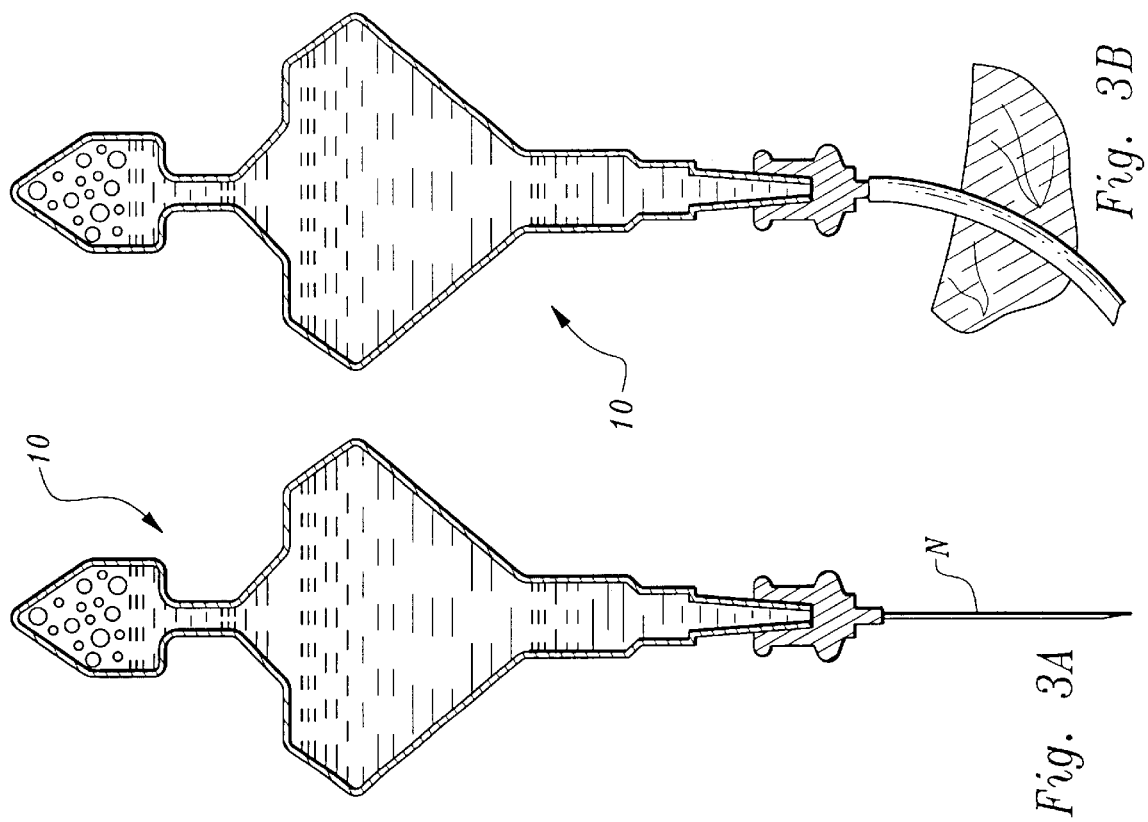
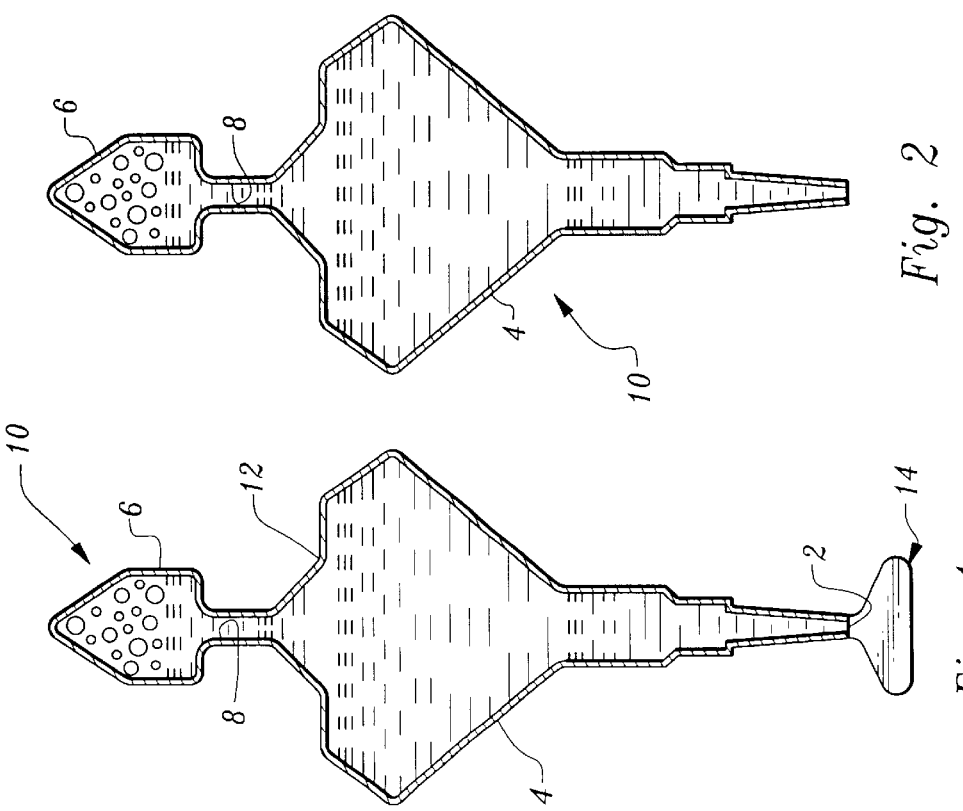

PLUNGERLESS SYRINGE: METHOD AND APPARATUS

FIELD OF THE INVENTION

The instant invention is directed to instrumentalities for therapeutic infusion. More specifically, the invention is directed to a plungerless syringe which is prefilled and delivers sterile fluid for therapeutic administration, and a method therefore.

BACKGROUND OF THE INVENTION

The following invention chronicles the ongoing evolution of applicant's further insights with respect to the following patents:

| Farris | 5,102,398 | Issued April 7, 1992 |
| Farris | 5,370,626 | Issued December 6, 1994 |
| Farris, et al. | 5,538,506 | Issued July 23, 1996 |

While these three technologies enumerated immediately hereinabove provide excellent therapeutic benefits, all have been shown to be quite excellent in respect of treatment of air entrained within a fluid during the Blow/Fill/Seal process. All of these patents sequester air from the fluid and excise the air from the fluid within the plungerless syringe prior to administration to a patient.

An additional nuance involves the recognition that when these syringes dock with other related infusion apparatus, such as a needle or catheter, the area of interconnection between the needle and/or catheter involves communication between these two elements at an interface. It has been observed that although a friction-type coupling will have been effected, the potential for minuscule albeit discernible quanta of air exists at the juncture between the infusion apparatus and the plungerless syringe. Although minuscule, microscopic or visible inclusions of air may have no discernible effect with respect to the vast majority of recipients of the infusion, applicant has developed further structure and method that treats the presence of this visible minute amount of air. Moreover, even small bubbles can be dangerous in very young, old or ill patients. For example, please see the appended article *Principals and Practice of Intravenous Therapy* at pages 53, 55 (Little, Brown and Company—fourth ed. 1987).

SUMMARY OF THE INVENTION

One salient attribute of the instant invention involves its contemplation of the small amount of air that can be found between a syringe needle or catheter juncture and its docking with the pre-filled plungerless syringes set forth above. Accordingly, an air chamber, partially filled with liquid, is provided extending from a back wall of a plungerless syringe. When the syringe is oriented in a vertical position with the air chamber at a highest elevation, after it has been docked with either a syringe needle or catheter, by vibrating the plungerless syringe (perhaps when coupled with first squeezing some liquid from the air chamber drawing some liquid into the coupling), any minute amounts of air encountered at the coupling situs will encourage the "coupling" air to migrate upwardly through the liquid filled major body portion of the plungerless syringe and into the air chamber along with the other air that has been sequestered which offsets the effect of the Blow/Fill/Seal process.

OBJECTS OF THE INVENTION

Accordingly, it is a primary object of the present invention to provide a new and novel apparatus for the safe infusion of liquids.

A further object of the present invention is to provide an apparatus as set forth above and a method associated therewith for manipulation of the syringe.

A further object of the present invention is to provide devices and methods as characterized above which take into account any small visible amounts of air which may initially exist between a syringe needle or catheter and a plungerless syringe.

A further object of the present invention is to provide a device as characterized above which is economical to manufacture and extremely safe to use.

A further object of the present invention is to provide device as characterized above and a method associated therewith which sequesters air from the juncture between a syringe and catheter or needle and allows the air to migrate to other air previously sequestered which was introduced during the Blow/Fill/Seal process.

Viewed from the first vantage point it is an object of this invention to provide a prefilled plungerless syringe comprising, in combination: a body having a back wall, a fluid outlet in fluid communication with an interior of the body, and a gas trap disposed on the back wall at an opposite end of the body from the fluid outlet, whereby any air existing at an interface with an infusion connector adapted to be coupled to the fluid outlet is to be received in the gas trap.

Viewed from a second vantage point it is an object of this invention to provide a method for sequestering gas from therapeutic fluid in a plungerless syringe having an air trap remote from a fluid exit, the steps including: docking the syringe with an infusion device at the fluid exit, orienting the syringe so that the air trap is at a higher elevation than the fluid exit, urging any gas from the infusion device and the syringe into the air trap, and injecting the therapeutic fluid.

These and other objects will be made manifest when considering the following detailed specification when taken in conjunction with the appended drawing figures.

BRIEF DESCRIPTION OF THE DRAWINGS

FIG. 1 is a sectional view taken along a long axis of the apparatus according to the present invention.

FIG. 2 is a view similar to FIG. 1 with a twist-off tab removed therefrom.

FIG. 3A is a view similar to FIG. 2 with a syringe needle deployed on a fluid outlet thereof.

FIG. 3B is a view similar to FIG. 2 with a catheter deployed on a fluid outlet thereof.

DESCRIPTION OF PREFERRED EMBODIMENTS

Figure 4A:
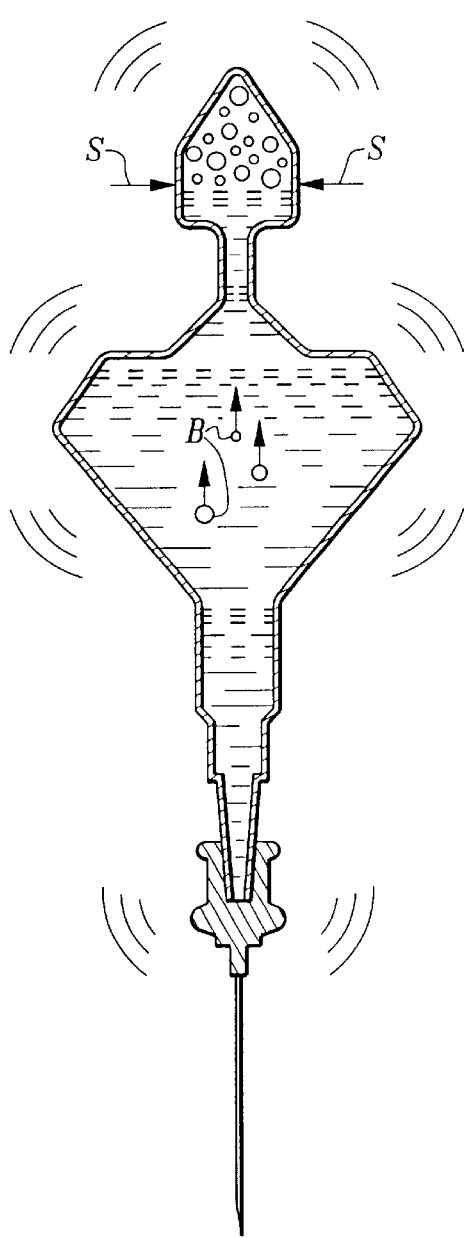
FIGS. 4A and 4B reflect the FIGS. 3A and 3B embodiments respectively showing air chamber squeezing and vibration in order to urge any bubbles that may exist between the interconnection of the syringe or catheter upwardly into the air chamber.

Considering the drawings, wherein like reference numerals denote like parts throughout the various drawing figures, reference numeral 10 is directed to the apparatus according to the present invention.

In its essence, the Blow/Fill/Seal, or plastic molded syringe 10 includes a major body 4 having at one extremity an outlet 2 for fluid configured as a luer coupling and a back wall 12 opposite from the fluid outlet 2. The back wall 12 includes an air passageway 8 preferably axially aligned with the fluid outlet and leading to an air chamber or trap 6. Note that as oriented in FIG. 1 with the air chamber 6 at a highest elevation compared to the luer coupling outlet 12, all gas and some liquid reside in the air chamber 6. The luer coupling fluid outlet 2 is initially occluded by means of a twist-off tab 14 so that during the Blow/Fill/Seal process, the device as shown in FIG. 1 is substantially fluid-filled when oriented in a vertical plane. Thus, the air trap 6, at its highest elevation with no air in the body 4 or air passageway 8 will contain gas and liquid.

Figure 4B:
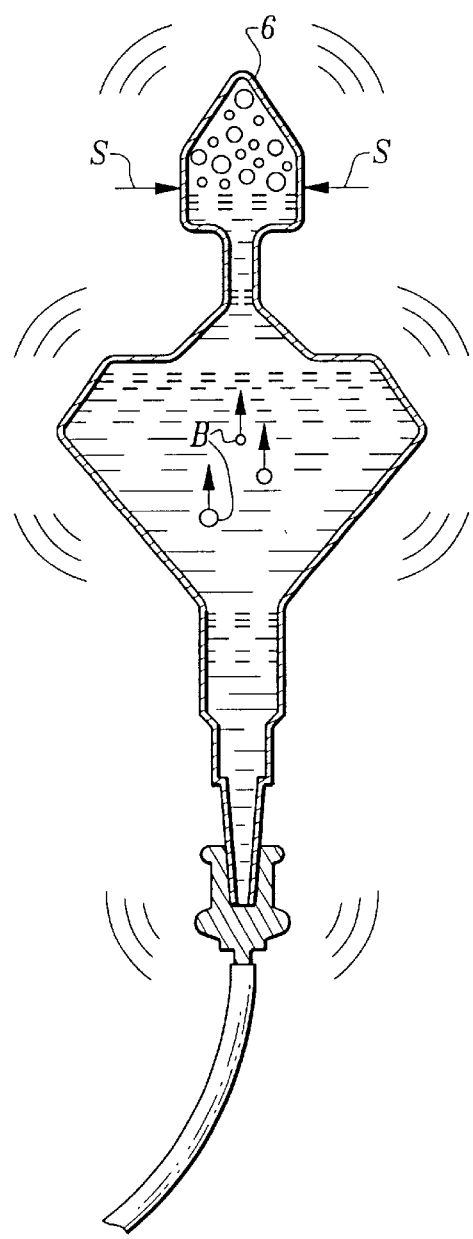

FIG. 2 reflects the FIG. 1 device with the twist-off tab 14 having been removed in preparation for docking with an infusion device, shown in FIGS. 3A and 3B as a syringe needle N (3A) or catheter coupling C (3B). After docking with the needle or catheter, FIGS. 4A and 4B reflect tapping, vibrating or another manner urging any gas that may have existed in the coupling area between the needle or catheter at the luer coupling to be urged upwardly through the body 4 and into the gas trap 6. For example, bubbles B can be urged upwardly by squeezing trap 6 as shown by arrows S of FIG. 4.

Figure 5:
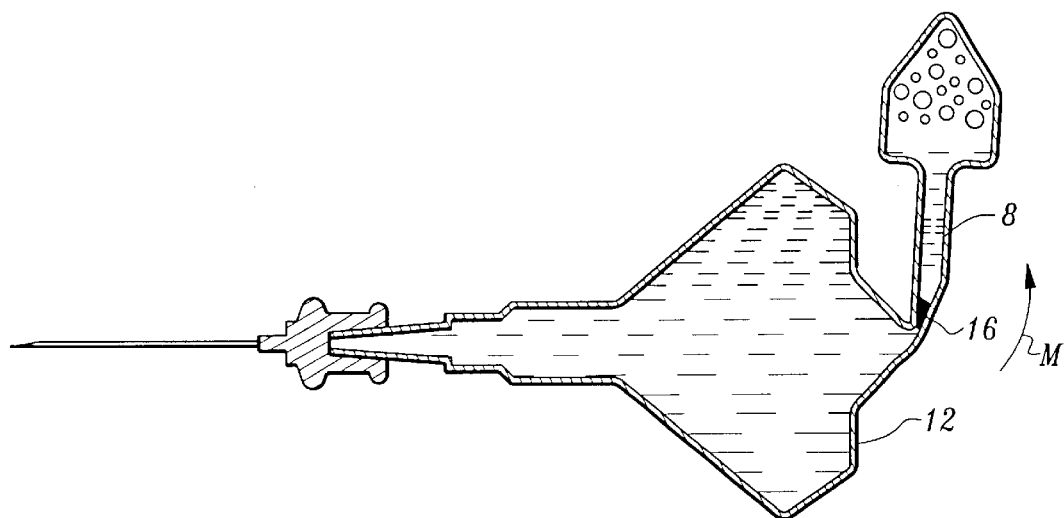
FIG. 5 shows the sequestration of the gas into a gas chamber and an air passageway communicating with a major body portion of the syringe sealed off.
Figure 6:
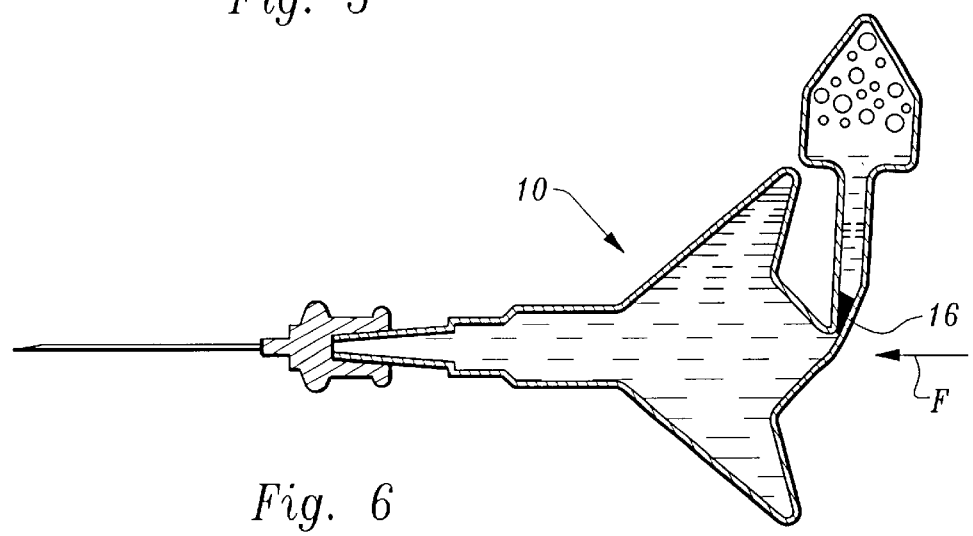
FIG. 6 shows the plunger having been depressed delivering the fluid.
Figure 7:
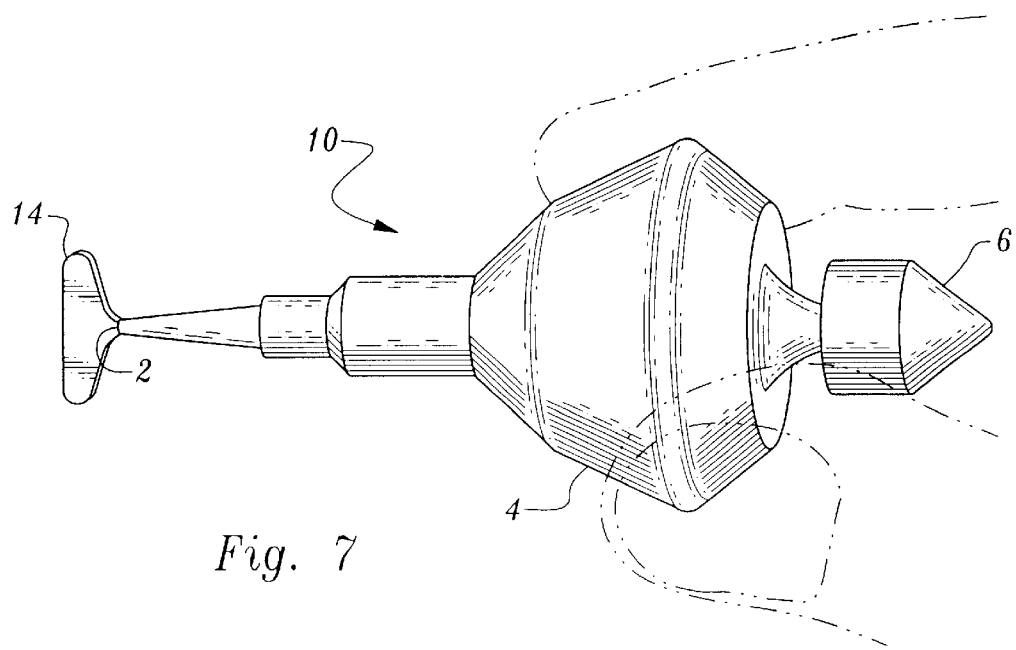
FIG. 7 is a perspective view of the apparatus.

With respect to FIG. 5, the air passageway has been rotated along the arrow M so that the passageway 8 will effectively be occluded at its juncture with the back wall 12. The reason for this is that the passageway 8 will have been pinched at site 16 where the passageway 8 extends from the back wall 12. Note the back wall 12 tapers to the passageway 8 to assist in migration of bubbles B into the trap 6. At this point, it is possible to inject the fluid contained within the syringe 10 by applying force along the direction of the arrow F shown in FIG. 6.

Note also the body 4 has a taper which widens as it extends from the fluid outlet 2 and then narrows as it approaches the passageway 8. This assists in migration of bubbles B.

Moreover, having thus described the invention, it should be apparent that numerous structural modifications and adaptations may be resorted to without departing from the scope and fair meaning of the instant invention as set forth hereinabove and as described hereinbelow by the claims.

I claim:

1. A prefilled plungerless syringe comprising, in combination:

a body having a back wall, a fluid outlet in fluid communication with an interior of said body, a gas trap disposed on said back wall at an opposite end of said body from said fluid outlet, whereby any air existing at a terminal extremity of said fluid outlet is to be received in said gas trap, and said body having a taper which widens as it extends from said fluid outlet and narrows as it approaches said gas trap on said back wall.

2. The syringe of claim 1 wherein said gas trap is connected to said back wall via a passageway which projects from said back wall and is in fluid communication with an interior of said syringe and said gas trap.

3. The syringe of claim 2 wherein said passageway is flexible to allow it to be pinched closed, sealing said gas trap from said body.

4. The syringe of claim 3 wherein said back wall tapers, narrowing towards said passageway.

5. The syringe of claim 4 wherein said syringe has a long axis and said outlet and passageway are aligned on said long axis at opposite ends of said body.

6. The syringe of claim 5 including a removeable tab at said fluid outlet.

* * * * *

UNITED STATES PATENT AND TRADEMARK OFFICE
CERTIFICATE OF CORRECTION

PATENT NO.    : 6,383,166 B1
DATED         : May 7, 2002
INVENTOR(S)   : Farris, Barry It is certified that error appears in the above-identified patent and that said Letters Patent is hereby corrected as shown below:

<u>Title page,</u>
Item [73], Assignee:, kindly change "Zephyr Cove, NV (US)" to No Assignee. This patent has not been assigned.

Signed and Sealed this

First Day of October, 2002

Attest:

Attesting Officer

JAMES E. ROGAN
Director of the United States Patent and Trademark Office